(12) United States Patent
Sevrain

(10) Patent No.: US 7,008,427 B2
(45) Date of Patent: Mar. 7, 2006

(54) INTER-VERTEBRAL DISC PROSTHESIS FOR RACHIS THROUGH ANTERIOR SURGERY THEREOF

(75) Inventor: Lionel C. Sevrain, West Palm Beach, FL (US)

(73) Assignee: OrthoPlex, LLC, Boston, MA (US)

(\*) Notice: Subject to any disclaimer, the term of this patent is extended or adjusted under 35 U.S.C. 154(b) by 2 days.

(21) Appl. No.: 10/296,392

(22) PCT Filed: May 25, 2001

(86) PCT No.: PCT/CA01/00739

§ 371 (c)(1),
(2), (4) Date: Sep. 15, 2003

(87) PCT Pub. No.: WO01/89428

PCT Pub. Date: Nov. 29, 2001

(65) Prior Publication Data

US 2004/0049279 A1 Mar. 11, 2004

Related U.S. Application Data

(60) Provisional application No. 60/264,309, filed on Jan. 29, 2001, provisional application No. 60/206,810, filed on May 25, 2000.

(51) Int. Cl.
*A61F 2/44* (2006.01)
*A61B 17/80* (2006.01)

(52) U.S. Cl. ..................... 606/71; 623/17.13
(58) Field of Classification Search .. 623/17.12–17.15, 623/17 FOR; 606/69 FOR, 70 FOR, 71 FOR
See application file for complete search history.

(56) References Cited

U.S. PATENT DOCUMENTS

| | | |
|---|---|---|
| 3,426,364 A | 2/1969 | Lumb |
| 3,547,114 A | 12/1970 | Haboush |
| 3,875,595 A | 4/1975 | Froning |
| 4,772,287 A | 9/1988 | Ray et al. |
| 4,863,477 A | 9/1989 | Monson |
| 4,904,260 A | 2/1990 | Ray et al. |
| 4,932,969 A | 6/1990 | Frey et al. |
| 5,002,576 A | 3/1991 | Fuhrmann et al. |
| 5,047,055 A | 9/1991 | Bao et al. |
| 5,171,280 A | 12/1992 | Baumgartner |
| 5,192,326 A | 3/1993 | Bao et al. |
| 5,258,031 A | 11/1993 | Salib et al. |
| 5,480,402 A | 1/1996 | Kim |
| 5,514,137 A | 5/1996 | Coutts |
| 5,556,431 A | 9/1996 | Büttner-Janz |

(Continued)

FOREIGN PATENT DOCUMENTS

DE   2263842 A1   7/1974

(Continued)

*Primary Examiner*—David H. Willse
(74) *Attorney, Agent, or Firm*—Burns & Levinson LLP; Frederick C. Williams; Yan Lan

(57) ABSTRACT

A disc prosthesis for use on a pair of adjacent vertebrae comprises upper and lower plates adapted to be mounted respectively to adjacent upper and lower vertebrae, typically using screws that extend through holes defined in the upper and lower plates and into the upper and lower vertebrae; a joint mechanism linking the upper and lower plates; and a damping system. The joint mechanism and the damping system are adapted to allow for biased relative movements between the upper and lower vertebrae.

15 Claims, 9 Drawing Sheets

U.S. PATENT DOCUMENTS

| | | |
|---|---|---|
| 5,562,738 A | 10/1996 | Boyd et al. |
| 5,603,713 A | 2/1997 | Aust et al. |
| 5,616,142 A | 4/1997 | Yuan et al. |
| 5,755,796 A | 5/1998 | Ibo et al. |
| 5,782,832 A | 7/1998 | Larsen et al. |
| 5,800,433 A | 9/1998 | Benzel et al. |
| 5,865,846 A | 2/1999 | Bryan et al. |
| 5,964,763 A | 10/1999 | Incavo et al. |
| 5,976,186 A | 11/1999 | Bao et al. |
| 6,001,130 A | 12/1999 | Bryan et al. |
| 6,022,376 A | 2/2000 | Assell et al. |
| 2003/0130661 A1 | 7/2003 | Osman |
| 2004/0019353 A1 | 1/2004 | Freid et al. |

FOREIGN PATENT DOCUMENTS

| | | |
|---|---|---|
| EP | 0282161 B1 | 8/1992 |
| EP | 0820731 B1 | 5/2003 |
| FR | 2723841 | 3/1996 |
| FR | 2 775 587 A1 * | 9/1999 |
| FR | 2775587 | 9/1999 |
| JP | 2000-210315 A | 8/2000 |
| WO | WO 94/04100 | 3/1994 |
| WO | WO 94/04100 A1 * | 3/1994 |
| WO | WO 99/00074 | 1/1999 |
| WO | WO 99/02108 | 1/1999 |
| WO | WO 00/04851 | 2/2000 |
| WO | WO 00/13620 | 3/2000 |

* cited by examiner

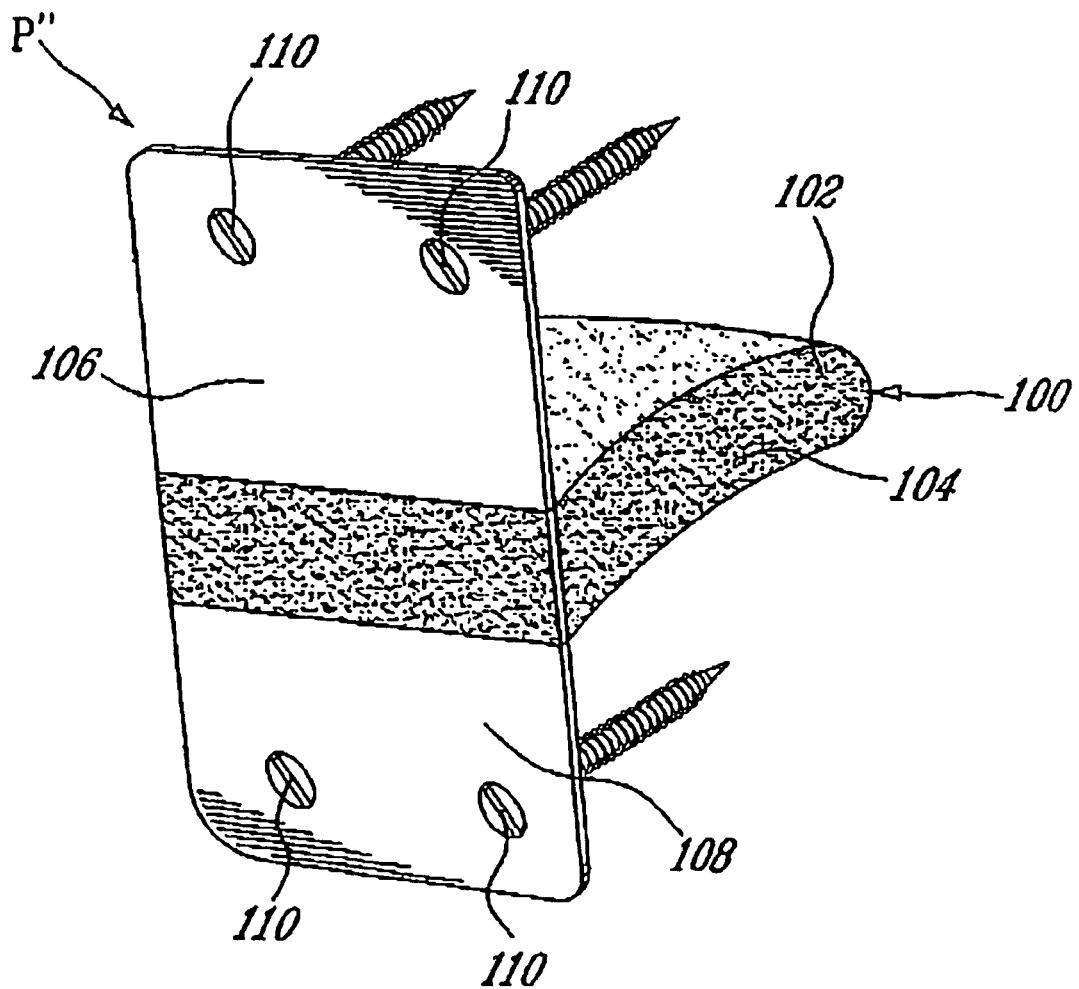
FIG_4

INTER-VERTEBRAL DISC PROSTHESIS FOR RACHIS THROUGH ANTERIOR SURGERY THEREOF

This application claims the benefit of U.S. Provisional Application No. 60/206,810, filed on May 25, 2000, and U.S. Provisional Application No. 60/264,309, filed on Jan. 29, 2001.

BACKGROUND OF THE INVENTION (a) Field of the Invention

The present invention relates to disc prostheses for the rachis and, more particularly, to disc prostheses installable through anterior surgery.

(b) Description of Prior Art

When a cervical disc is anteriorly removed (e.g. using the Smith-Robinson surgical technique) from between two adjacent vertebrae, for instance to liberate roots and/or medulla which are compressed by a degenerated disc or to remove a damaged disc, it is known to fuse both these vertebrae together (i.e. osteosynthesis by way of an anterior cervical plate) to provide stability to the rachis although this results in loss of mobility and damping. This rigidification (on one or more successive discs) induces greater stresses to the natural discs located adjacently above and below the removed disc(s) thereby causing a premature ageing of these natural discs, and also creates experimental conditions for the formation of discal hernias on the adjacent levels.

U.S. Pat. No. 5,258,031 issued to Salib et al. discloses a non-compressible prosthetic disc of the ball-and-socket type where the male and female members are fixed to respective upper and lower plates that are secured to adjacent upper and lower vertebrae by way of screws. The disc prosthesis is thus adapted to replace a natural disc of the lumbar spine and it provides six degrees of freedom such as to substantially reproduce the normal intervertebral pivoting movements, except compression.

U.S. Pat. Nos. 5,865,846 and 6,001,130 both issued to Bryan et al. respectively on Feb. 2 and Dec. 14, 1999 are similar (although the latter is more detailed) in each teaching a disc prosthesis comprising a resilient body, of varying stiffness from a substantially stiff exterior annular gasket to a relatively supple central nucleus. The disc prosthesis is adapted to be installed in the intervertebral space with concave-convex elements at least partly surrounding the resilient body to retain it in the intervertebral space. These elements include a pair of L-shaped supports mounted to respective adjacent upper and lower vertebrae with screws that extend through the vertical leg or wing sections of the L-shaped supports. The horizontal leg or wing sections of the L-shaped supports extend in the intervertebral space and surround the resilient body on opposite upper and lower sides thereof. It is possible for the vertical and horizontal leg sections of each L-shaped support to be hinged together at the anterior faces of the vertebrae but only for adjustment during installation of the prosthesis and not to act as a hinge after installation. There may be two or more disc prostheses disposed in series between three or more adjacent vertebrae.

U.S. Pat. No. 5,755,796 issued on May 26, 1998 to Ibo et al. discloses a cervical intervertebral disc prosthesis also of the ball-and-socket type which allows for a pivotal movement between two adjacent vertebrae.

U.S. Pat. No. 5,556,431 issued on Sep. 10, 1996 to Büttner-Janz also teaches a disc prosthesis somewhat similar in function to that of aforementioned U.S. Pat. No. 6,001,130, although its two anchoring plates do not extend along the anterior faces of the vertebrae. The screws holding the anchoring plates to the vertebrae are engaged in the vertebrae from the intervertebral face thereof. The prosthesis core has a peripheral rim to limit its range of movements. Anchoring teeth are provided on the plates for penetrating, under load, the vertebrae.

U.S. Pat. No. 3,426,364 issued on Feb. 11, 1969 to Lumb describes a spinal prosthesis to replace natural vertebrae which had to be removed. A spring member may extend in the prosthesis.

U.S. Pat. No. 5,562,738 issued to Boyd et al. on Oct. 8, 1996 is similar to above-described U.S. Pat. No. 5,258,031.

U.S. Pat. No. 5,171,280 issued on Dec. 15, 1992 to Baumgartner discloses an inter-vertebral prosthesis which includes a coiler body able to rotate onto a fixed base with a flexible elastic hollow body extending from the coiler body and adapted to receive therein a filling medium through a valve. The prosthesis, once implanted and filled with an incompressible medium, is able to absorb radial forces exerted upon the periphery via the incompressible medium in the elastic hollow body. The prosthesis can be inserted in the intervertebral region through a small opening.

U.S. Pat. No. 3,875,595 issued on Apr. 8, 1975 to Froning discloses an inter-vertebral disc prosthesis in the form of a collapsible plastic bladder-like member that has the shape of the nucleus pulposis of a natural inter-vertebral disc. After removal of the degenerated natural nucleus pulposis, the prosthesis, in its collapsed position, is inserted through a stem and into the inter-somatic space, and a filling medium is then inserted through the stem and into the prosthesis to inflate it to a natural form. The stem is then severed just upstream of a valve thereof such that the valve remains implanted with the prosthesis.

U.S. Pat. No. 4,772,287 and U.S Pat. No. 4,904,260 which issued respectively on Sep. 20, 1998 and Feb. 27, 1990 both in the names of Ray et al. describe the implantation of two prosthetic disc capsules side-by-side into a damaged disc of a human spine.

U.S. Pat. No. 6,022,376 issued on Feb. 8, 2000 to Assell et al. discloses a capsule-shaped prosthetic spinal disc nucleus for implantation into a human intradiscal space, made of a substantially inelastic constraining jacket surrounding an amorphous polymer core with the constraining jacket having a fixed maximum volume and defining a height, while the amorphous polymer core fills an initial volume of the constraining jacket and develops an internal pressure.

U.S. Pat. No. 5,192,326 and U.S. Pat. No. 5,047,055 which issued respectively on Mar. 9, 1993 and Sep. 10, 1991 both in the name of Bao et al. teach a prosthetic nucleus adapted to be implanted in the intersomatic space of a spine and which is formed of a multiplicity of hydrogel beads which are covered by a semi-permeable membrane. This prosthetic nucleus is adapted to conform, when hydrated, to the general shape of the natural nucleus. The prosthetic nucleus is surrounded by the natural annulus fibrous. Vertebral end plates cover the superior and inferior faces of the prosthetic nucleus.

U.S. Pat. No. 4,863,477 issued on Sep. 5, 1989 to Monson discloses a synthetic inter-vertebral disc prosthesis which is made of two halves which, after having been joined together, are implanted in the intersomatic space in place of a removed natural disc. A fluid, such as a saline solution, is then injected into the interior cavity of the prosthesis to provide the required amount of resiliency in the disc prosthesis thereby restoring proper vertebral spacing and facilitating flexibility of the spine.

U.S. Pat. No. 5,976,186 issued on Nov. 2, 1999 to Bao et al. discloses a hydrogel inter-vertebral disc nucleus adapted to be inserted in the inter-somatic space through an opening in the natural annulus for replacing the natural nucleus. The hydrogel disc is adapted to essentially fill the inter-vertebral nuclear disc cavity upon absorbing sufficient water from the body fluids.

SUMMARY OF THE INVENTION

It is therefore an aim of the present invention to provide a novel disc prosthesis for use on the human rachis.

It is also an aim of the present invention to provide a disc prosthesis adapted to installed on the rachis through anterior surgery.

It is a further aim of the present invention to provide a disc prosthesis that allows for relative movements between adjacent vertebrae in addition to provide damping thereto.

Therefore, in accordance with the present invention, there is provided a disc prosthesis for use on a pair of adjacent vertebrae, comprising upper and lower plate means adapted to be mounted respectively to adjacent upper and lower vertebrae, joint means linking said upper and lower plate means, and damping means, said joint means and said damping means being adapted to allow for limited biased relative movements between the upper and lower vertebrae.

More particularly, said joint means comprise a flexible pouch means located at least mostly in an intersomatic space defined between the adjacent vertebrae, said damping means including a damping fluid, such as a hydrogel, located in said pouch means.

The upper and lower plate means comprise upper and lower extensions of said pouch means extending anteriorly of the vertebrae and adapted to be secured anteriorly to the vertebrae using threaded fasteners. Holes are defined in the extensions to receive the fasteners with reinforcement eyelets being provided at said holes.

Typically, the flexible pouch means comprises a deformable jacket that has a bi-concave nucleus-like shape for conforming engagement thereof with endplates of the vertebrae. Also, the deformable jacket has an intrinsic resiliency, or memory, to provide said jacket with a tendency to maintain said bi-concave nucleus-like shape during displacements of said jacket in the intersomatic space and so maintain contact between said jacket and the endplates of the vertebrae.

The damping means comprise a bi-concave hydrogel mimicking the natural shape of a human disc (e.g. for a cervical disc: 16, 18 or 20 mm depth×6, 8 or 10 mm height). The upper and lower plates are frontal, extra-spinal and pre-somatic, upper and lower extensions extending respectively from the antero-superior and antero-inferior edges of the jacket. These upper and lower extensions are intended to be used as anchors on the anterior faces of the two adjacent vertebrae.

In another more specific embodiment, the joint means comprise a substantially V-shaped joint extending at least partly in an intersomatic space defined between the adjacent vertebrae, said joint having upper and lower arms adapted to pivot relative to each other thereby allowing for at least one of an extension and a contraction movement between the upper and lower vertebrae, and said damping means being adapted to act on said joint. Typically, the upper and lower arms are rigidly connected respectively to said upper and lower plate means.

The upper and lower plate means are adapted to extend anteriorly of the vertebrae, said upper and lower plate means defining holes, threaded fasteners being provided for engagement through said holes and anteriorly into the vertebrae for securing said plate means to the vertebrae.

Generally, the upper and lower arms are posteriorly connected by a hinge within the intersomatic space. The damping means comprises at least one spring, for instance located within the intersomatic space, acting on said upper and lower arms for biasing said joint towards an at rest position thereof.

The upper and lower arms are posteriorly connected by a hinge within the intersomatic space, said damping means comprising at least one spring acting on said upper and lower arms. The spring may take the form of a biased U-shaped sheet disposed between said upper and lower arms and anteriorly of said hinge, said sheet being connected at upper and lower free ends thereof respectively to said upper and lower arms.

In a further more specific embodiment, the joint means comprise an anterior guillotine-type joint having engaged upper and lower members adapted for sliding relative movements therebetween, and said damping means being adapted to act on said joint. Typically, the upper and lower plate means are adapted to extend anteriorly of the vertebrae, said upper and lower plate means being integrally connected respectively to said upper and lower members of said joint.

Specifically, one of said upper and lower members defines a U-shaped recess with the other one of said upper and lower members defining an extension adapted to be slidably received in said recess such that said upper and lower members are slidably displaceable along direction substantially within a plane of said plate means. The U-shaped recess is provided laterally with guideways extending parallel to said direction and slidably receiving side longitudinal edges of said extension for allowing slidable relative movement between said upper and lower members.

BRIEF DESCRIPTION OF THE DRAWINGS

Having thus generally described the nature of the invention, reference will now be made to the accompanying drawings, showing by way of illustration a preferred embodiment thereof, and in which:

FIG. 4 is a schematic perspective view of a disc prosthesis in accordance with a third embodiment of the present invention.

DESCRIPTION OF THE PREFERRED EMBODIMENTS

As discussed hereinabove, when a cervical disc is anteriorly removed (e.g. using the Smith-Robinson surgical technique) from between two adjacent vertebrae, for instance to liberate roots and/or spinal cord which are compressed by a degenerated disc or to remove a damages disc, it is known to fuse both these vertebrae together (i.e. osteosynthesis by way of an anterior cervical plate) to provide stability to the rachis although this results in loss of mobility and damping. This rigidification (on one or more successive discs) induces greater stresses to the natural discs located adjacently above and below the removed disc(s) thereby causing a premature ageing of these natural discs, and also creates experimental conditions for the formation of discal hernias on the adjacent levels.

To overcome at least in part these disadvantages, the present invention proposes a new disc prosthesis or prosthetic implant which, in addition to providing stability by connecting the two adjacent vertebrae, allows for some relative movements therebetween, e.g. flexion and extension, and for damping when subjected to axial loads.

Figure 1:
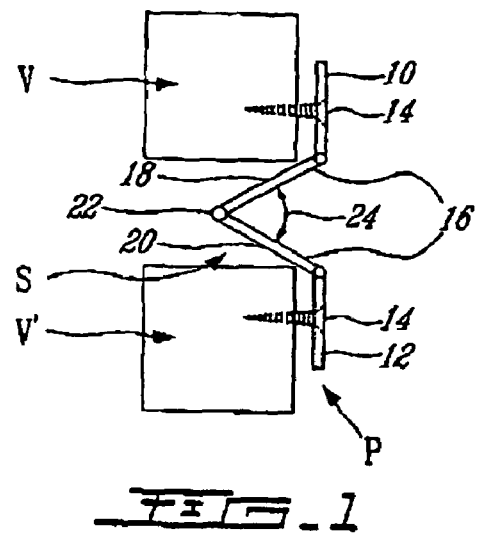
FIG. 1 is a schematic side elevational view of a disc prosthesis in accordance with a first embodiment of the present invention and shown mounted to a pair of adjacent vertebrae.
Figure 1A:
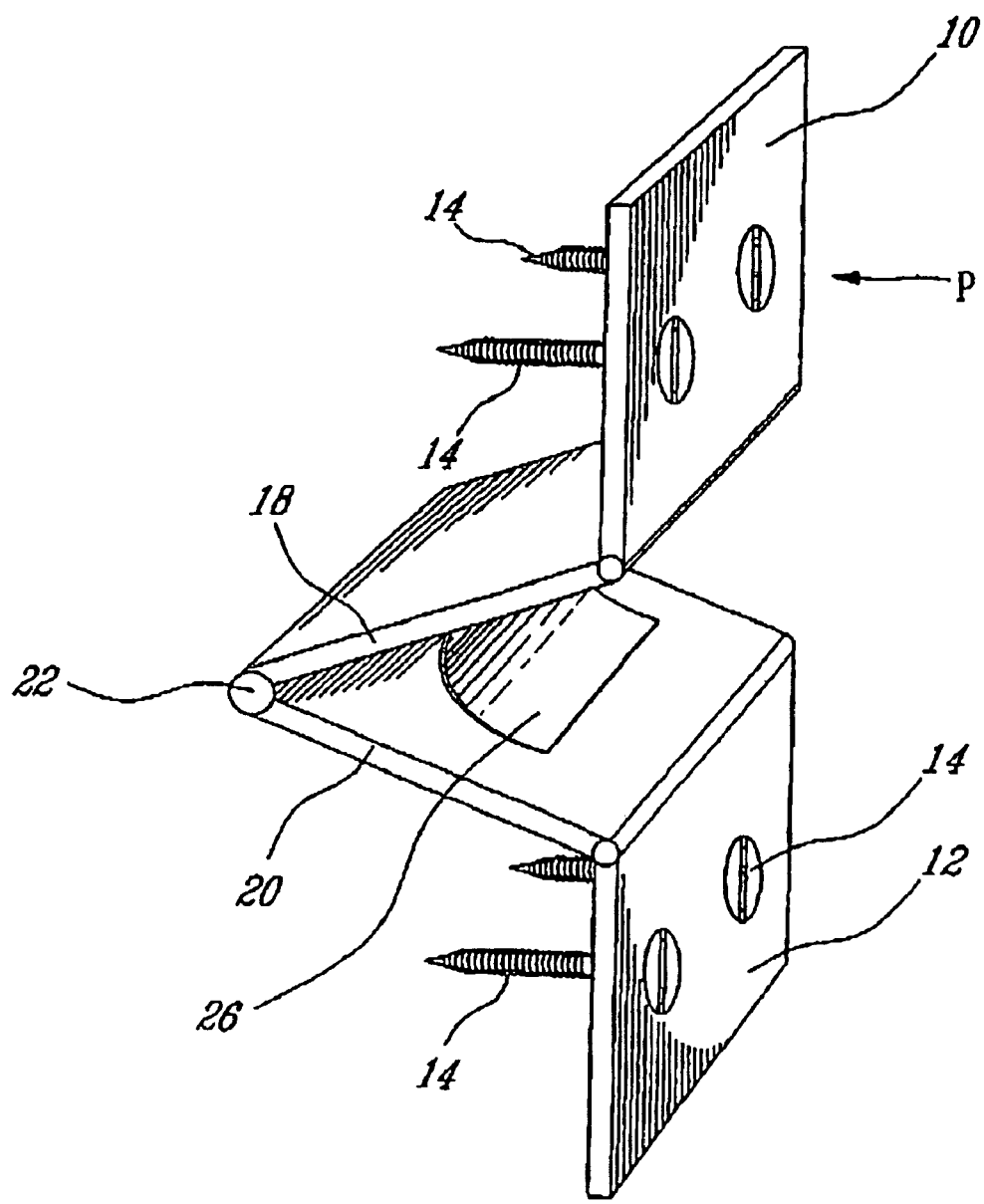
FIG. 1A a schematic perspective view of the disc prosthesis of FIG. 1.
Figure 1B:
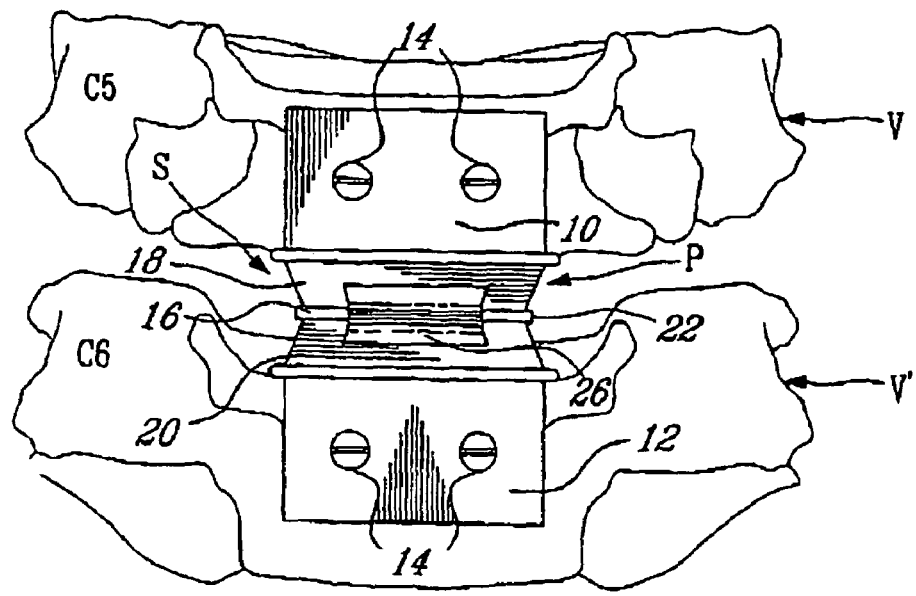
FIGS. 1B and 1C are schematic front and side elevational views of the disc prosthesis of FIG. 1A shown in an extended position thereof between the adjacent vertebrae.
Figure 1C:
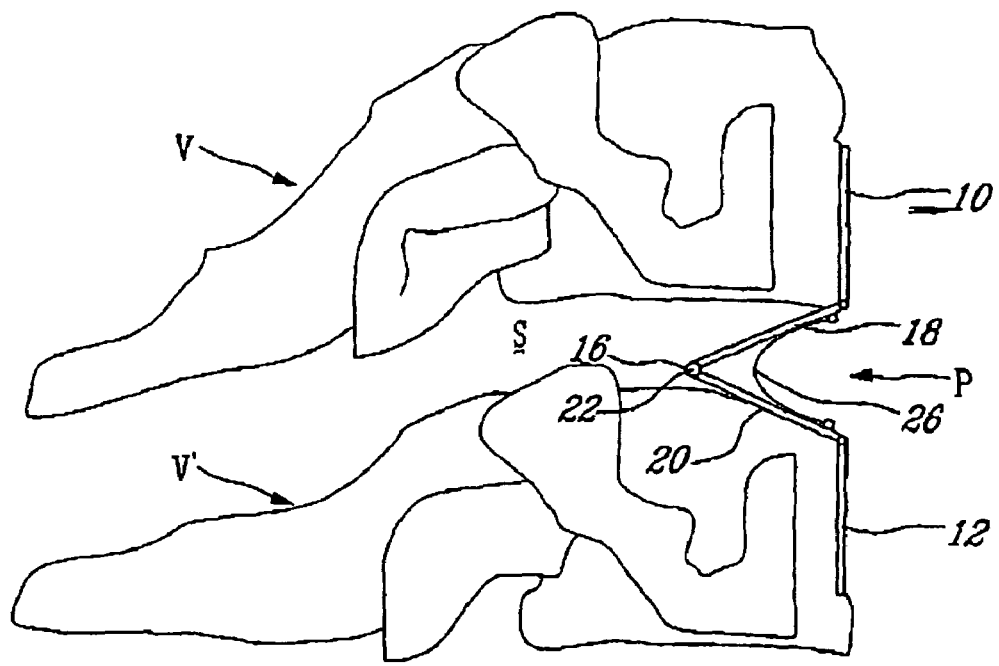
Figure 1D:
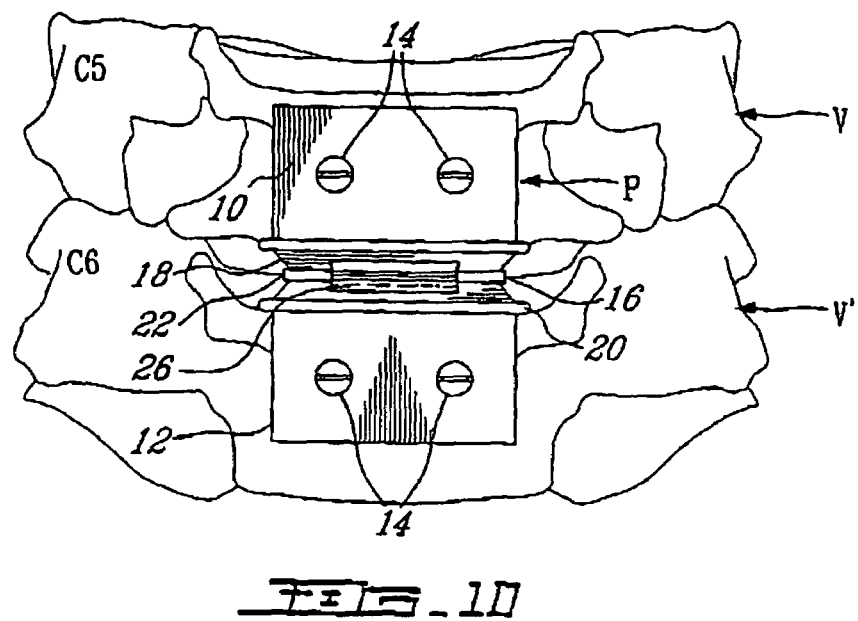
FIGS. 1D and 1E are schematic front and side elevational views of the disc prosthesis of FIG. 1A shown in a flexed position thereof between the adjacent vertebrae.
Figure 1E:
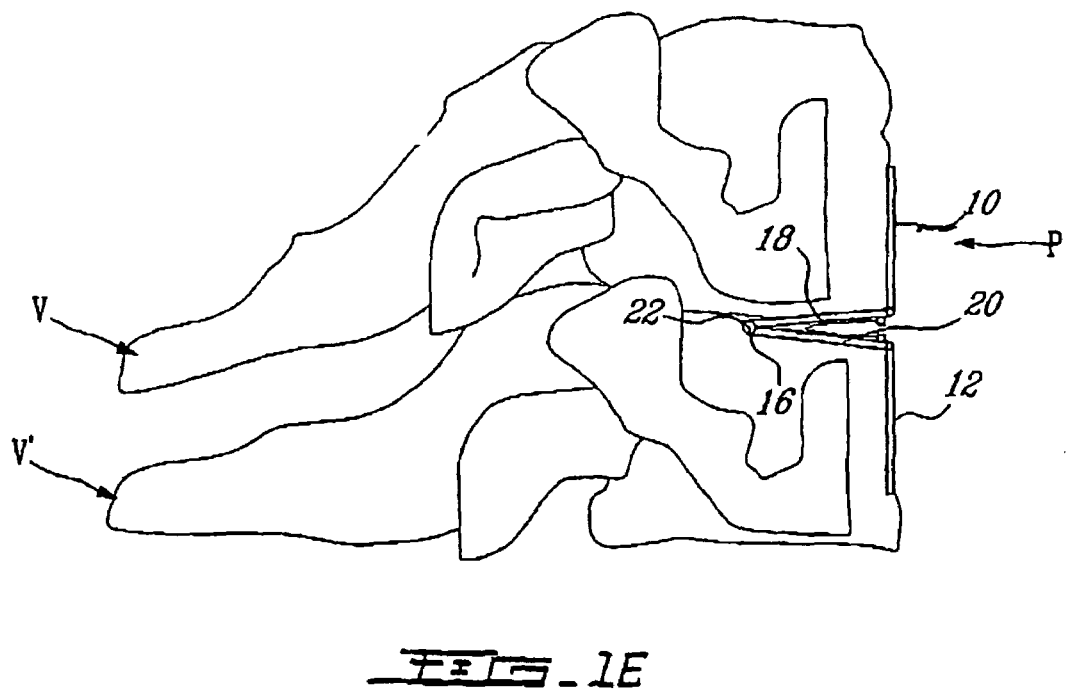

More particularly, the disc prosthesis P illustrated in FIGS. 1 and 1A comprises upper and lower anchoring plates 10 and 12, respectively, which are adapted to be secured with screws 14 to anterior faces of adjacent upper and lower vertebrae V and V'. The prosthesis P also includes a joint 16 connected to, and between, both plates 10 and 12 to link both vertebrae V and V' in a stable manner and further providing damping characteristics to the prosthesis P and relative movements between the vertebrae V and V'. The joint 16 comprises a pair of upper and lower arms 18 and 20, respectively, which define a V-shaped configuration extending rearwardly from an anterior face of the vertebrae V and V' and into the intervertebral space S defined vertically between the vertebrae V and V'. The upper and lower arms 18 and 20 can pivot such as with a hinge, at posterior ends thereof, i.e. at the apex 22 of the joint 16. The arms 18 and 20 of the joint 16 are biased, as per arrows 24 in FIG. 1, towards an open or expanded position thereof, for instance by way of a spring 26 (best shown in FIGS. 1A and 1C) in the form of a arcuately folded sheet, such that upon a movement of the rachis which brings the two vertebrae V and V' closer together, the joint 16 closes against the spring force, the arms 18 and 20 pivoting towards each other about the apex 22, with the spring 26 being adapted to return the joint 16 to its at rest position once the effort made by the user that moves the rachis is released.

More than one spring may be used for maintaining, at rest, the joint 16 in an intermediate position, i.e. in a "floating" position such that the joint 16 is capable of opening or closing, with the spring forces always bringing it back to its at rest position. The upper and lower arms 18 and 20 of the joint 16 may be integral with the upper and lower plates 10 and 12, respectively.

The joint 16 substantially ensures three functions of the natural disc: stability by providing continuity between the adjacent vertebrae V and V', damping in the axial plane: and flexion-extension movements in the sagittal plane. Depending on the material used for making the joint 16 (biocompatible or not), the joint 16 may be housed in a sealed chamber. The prosthesis P is, for instance, well adapted for the use on the cervical rachis.

In FIGS. 1B to 1E, the joint 16 is shown in extended and flexed positions thereof.

The joint 16 can also comprise one or more dynamometers; a system of one or more fluid-based dampers, i.e. with liquid(s) or gas(es); a bag to replace the natural disc's annulus, which is filled with a liquid, or other appropriate substance, having a proper viscosity index to replace the nucleus pulposus; etc.

Figure 2:
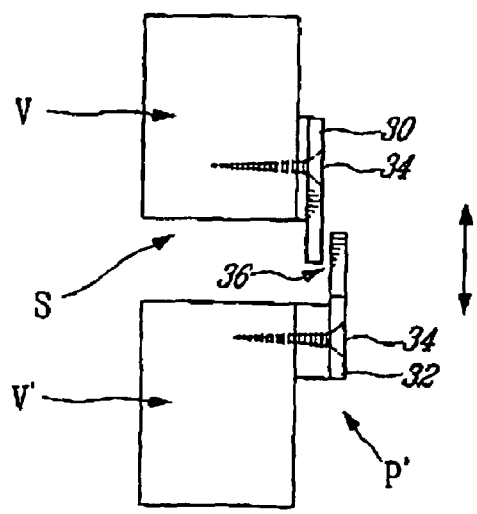
FIG. 2 is a schematic side elevational view of a disc prosthesis in accordance with a second embodiment of the present invention and shown mounted to a pair of adjacent vertebrae.
Figure 3:
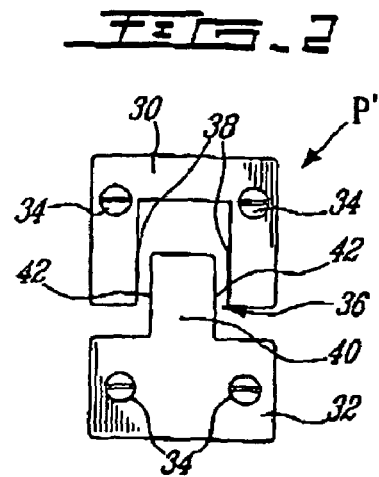
FIG. 3 is a schematic front elevational view of the disc prosthesis of FIG. 2.

In FIGS. 2 and 3, there is shown a second embodiment of a disc prosthesis P' also in accordance with the present invention and which has a cigar-cutter configuration, being located completely anteriorly of the upper and lower vertebrae V and V such as to provide for translational displacements along an axial plane between the vertebrae V and V (as opposed to the pivoting movement of the first disc prosthesis P of FIGS. 1 and 1A).

The second prosthesis P (see FIGS. 2, 2A and 3) comprises upper and lower anchoring plates 30 and 32, respectively, which are adapted to be secured with screws 34 to anterior faces of the adjacent upper and lower vertebrae V and V'. This second prosthesis P' may also be used on the various vertebrae of the rachis, including advantageously on the cervical rachis. The prosthesis P' also includes a joint 36 connecting both plates 30 and 32 to link both vertebrae V and V' in a stable manner and further providing damping characteristics to the prosthesis P' and relative movements between the vertebrae V and V'. The upper plate 30 may be inverted U-shaped and define side guideways 38 while the lower plate 32 defines an extension 40 that is slidably engaged at its longitudinal sides 42 in the guideways 38. A stop member 37 as shown in FIG. 2A, is provided for preventing the complete withdrawal of the lower plate 32 from the upper plate 30 in the event of hyperextension by the patient.

Figure 2A:
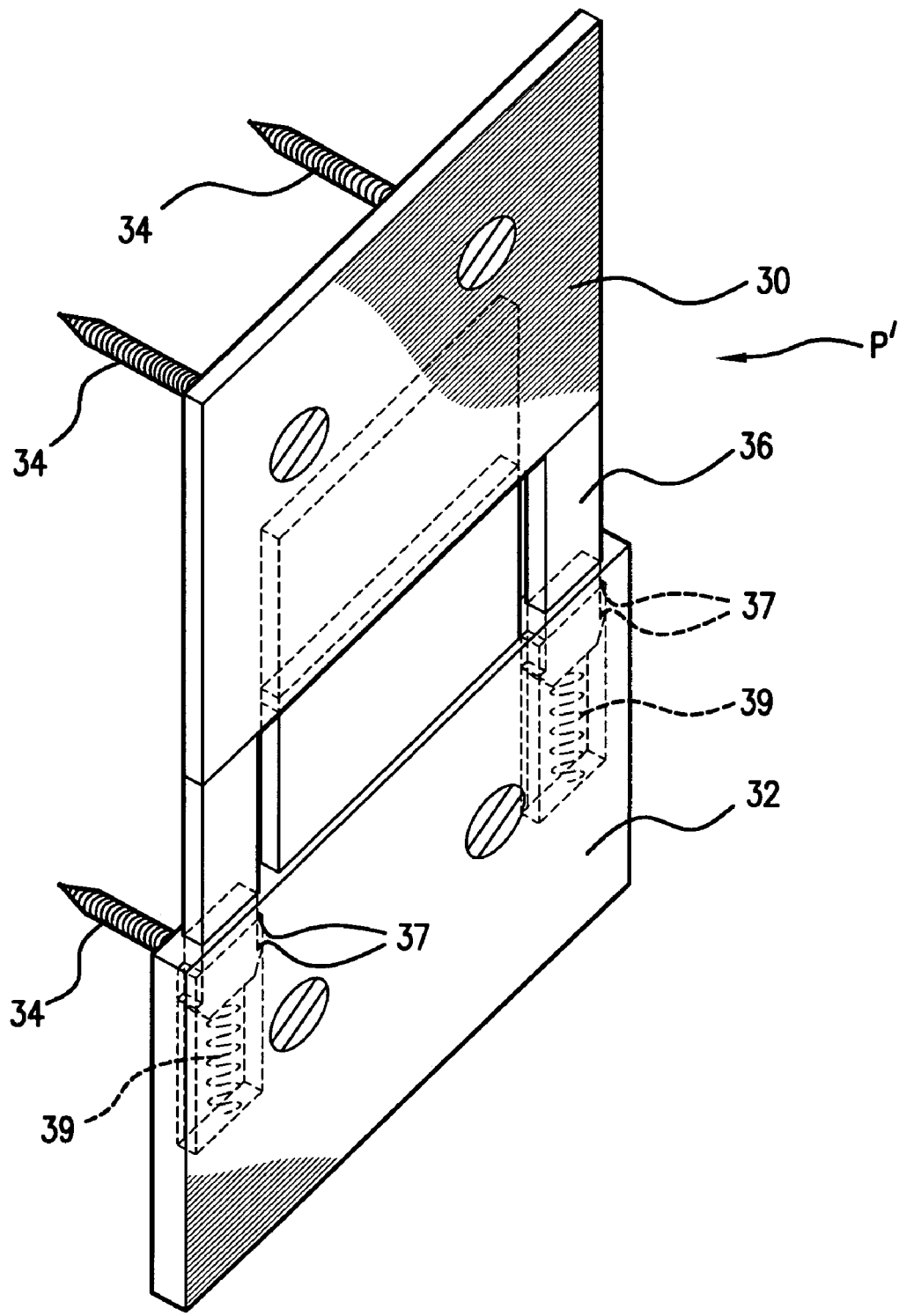
FIG. 2A a schematic perspective view of the disc prosthesis of FIG. 2.
Figure 2B:
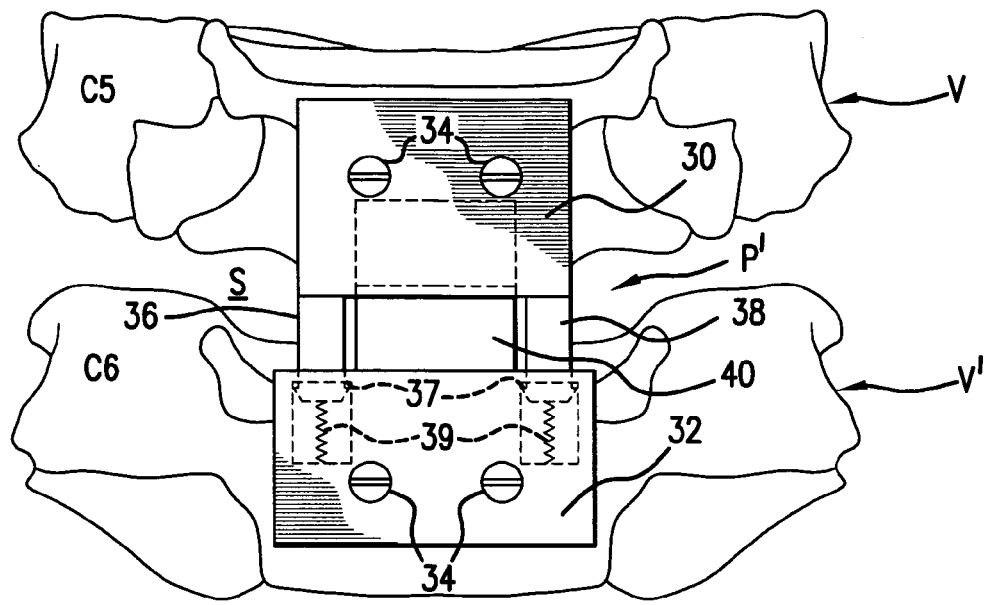
FIGS. 2B and 2C are schematic front and side elevational views of the disc prosthesis of FIG. 2A shown in an extended position thereof between the adjacent vertebrae.
Figure 2C:
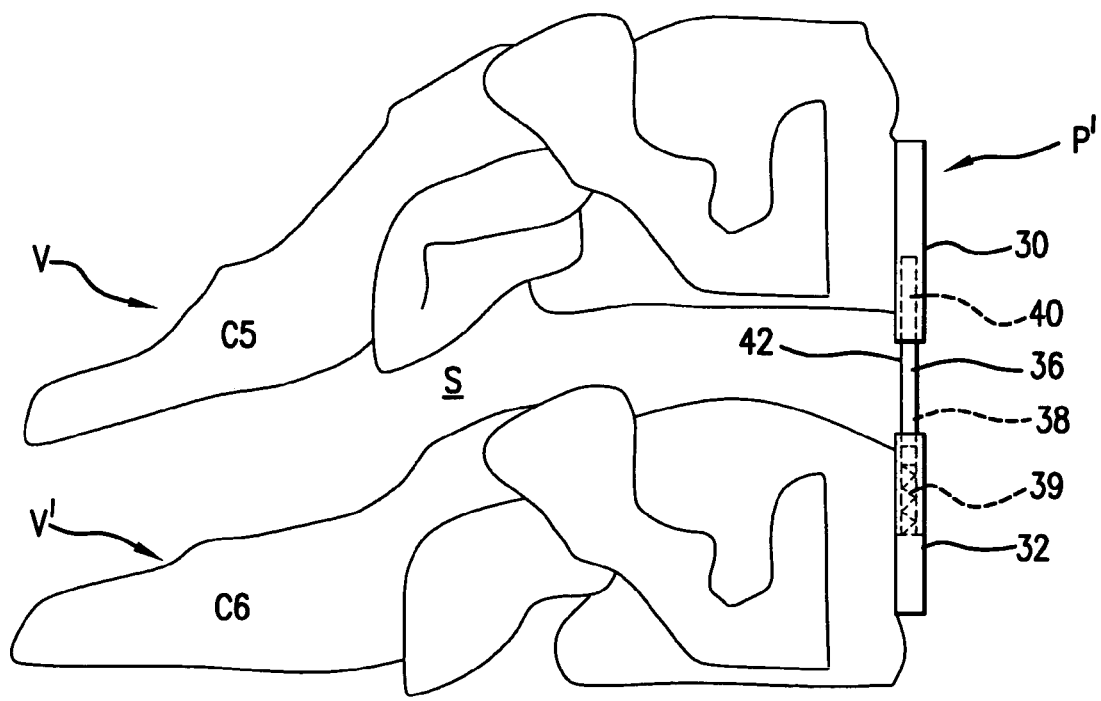
Figure 2D:
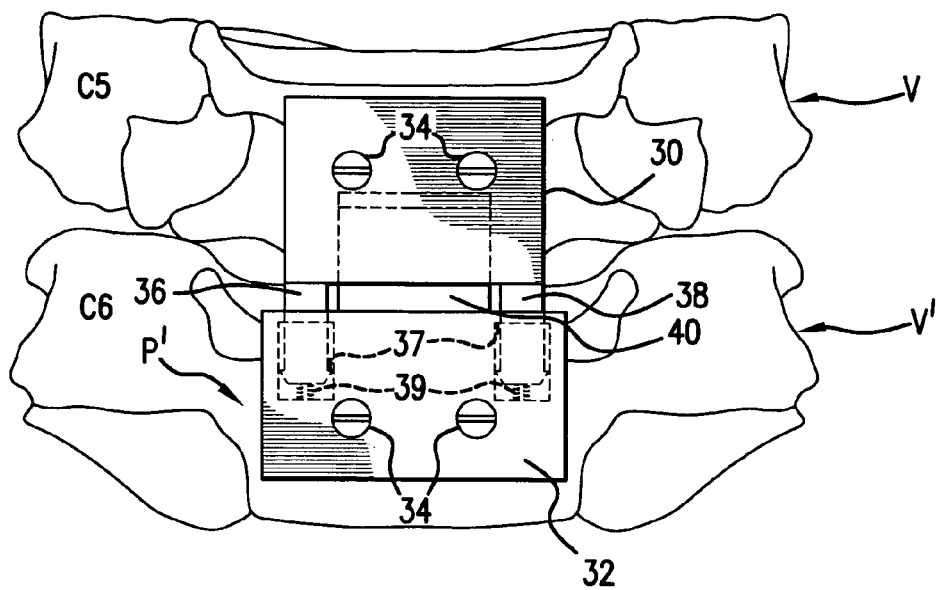
FIGS. 2D and 2E are schematic front and side elevational views of the disc prosthesis of FIG. 2A shown in a flexed position thereof between the adjacent vertebrae.
Figure 2E:
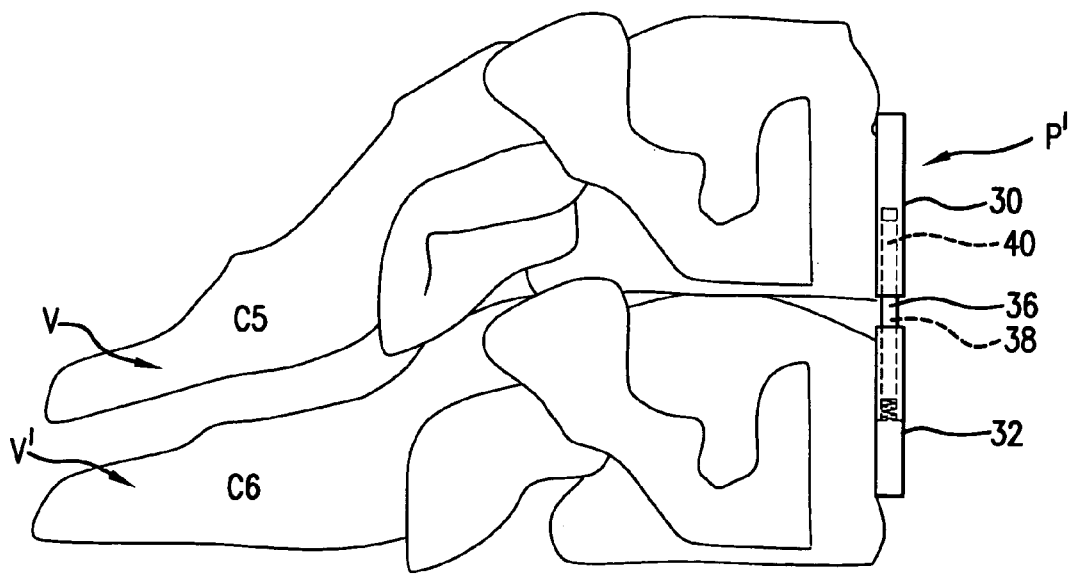

As in a cigar cutter, a spring 39, as shown in FIG. 2A, is preferably provided between the upper and lower plates 30 and 32, for instance in the guideways 38, such that the prosthesis P is biased towards its extended position.

Alternatively, the spring effect may be provided in the intervertebral space S defined between the vertebrae V and V', i.e. posteriorly of the plates 30 and 32, such a by a coil spring extending vertically between, and linking, both vertebrae V and V', or by a damping unit consisting for example of a bag containing a fluid (liquid or gaseous). Also, the plates 30 and 32 could include a substantially horizontal posterior intersomatic extension, located in the space S and between which a bias system, e.g. a spring or fluid damper, would be provided.

For the cervical rachis, the plates 30 and 32 are concave to respect the natural cervical lordosis of the anterior wall of the cervical spine and to guide harmonious flexion-extension movements.

In FIGS. 2B to 2E, the joint 36 is shown in extended and flexed positions thereof.

Figure 5:
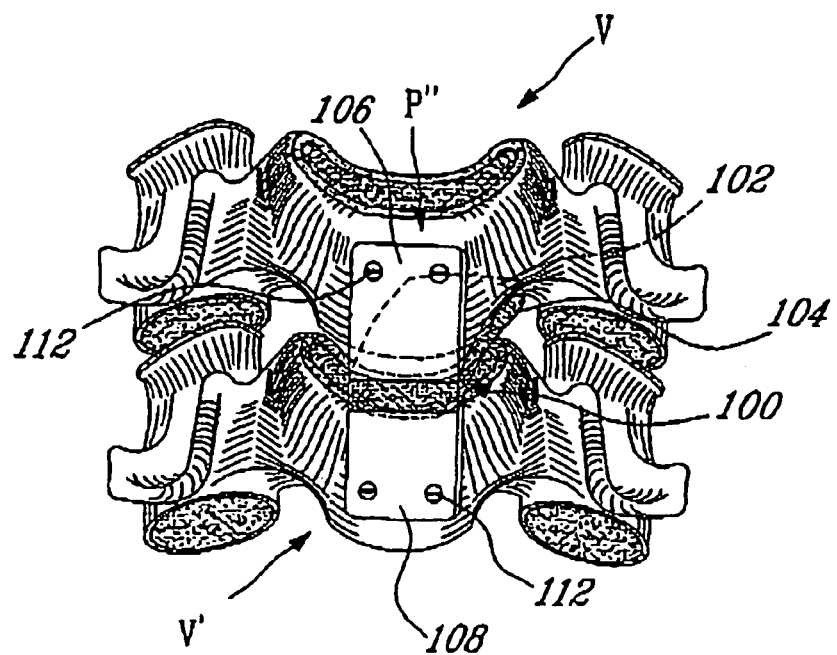
FIGS. 5 and 6 are respectively front perspective and side elevational views of the disc prosthesis of FIG. 4, shown mounted to a pair of adjacent vertebrae.
Figure 6:
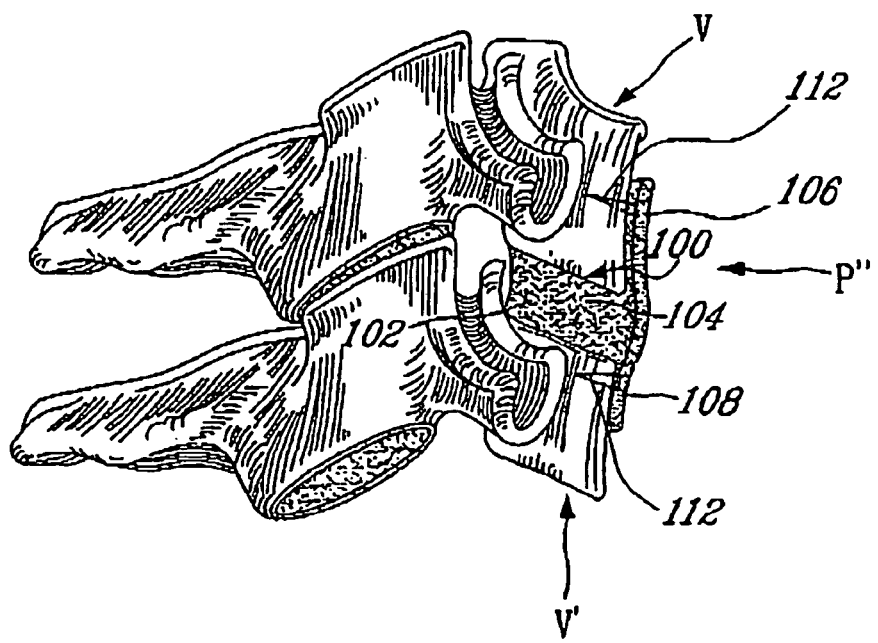

In FIGS. 4 to 6 which show a third embodiment also in accordance with the present invention, a further disc prosthesis P''' is illustrated and is, in fact, a one-piece tissue jacket 100 defining a posterior bi-concave constraining chamber 102 adapted to receive therein a hydrogel 104 that acts as a damper, with anterior frontally extending upper and lower extensions 106 and 108, respectively, adapted to be anchored to the anterior faces of the facing upper and lower vertebrae V and V' with screws 112 that extend through reinforced eyelets 110.

More particularly, the bi-concave hydrogel 104 of the joint of disc prosthesis pH conforms to or mimics the natural shape of a cervical disc (16, 18 or 20 mm depth.times.6, 8 or 10 mm height) and is surrounded or coated with the deformable constraining jacket 100 located in an intra-spinal inter-somatic space. The pair of frontal, extra-spinal and pre-somatic, upper and lower extensions 106 and 108 extend respectively from the antero-superior and antero-inferior intersomatic extension 101 of the jacket 100.

As to the nucleus core 104 of this third disc prosthesis P'', it is made of a hydrogel, which is non-biodegradable and is chemically reticulated by covalent bonds, and which has visco-elastic properties that are similar to those of the natural nucleus pulposus such as to counterbalance or offset the external hydrostatic pressure which is exerted thereon. The hydrogel has a swelling or inflating capability in an aqueous solution of about 85 to 95%, at equilibrium (WG). The hydrogel can be a terpolymer formed of: (a) a methacrylamide N-substitute, for instance [N-2 (hydroxypropyl methacrylamide)] (HPMA); (b) a hydroxy alkyl methacrylate ester, for instance 2-hydroxyethyl methacrylate (HEMA); and (c) a di- or tri-ethylene glycol dimethacrylate (DEGDMA or TEGDMA).

While it is manufactured, the hydrogel 104 is dehydrated and inserted in the intervertebral cavity. Then, it is manually rehydrated in an aqueous solution by using a needle puncture through the coating jacket 100 until its maximal swelling capability (WG). The hydrogel is prepared in such a way that WG corresponds to a pre-selected specific volume of the inter-vertebral bi-concave chamber 102 in order to obtain the adequate pressure. This hydrogel forming the nucleus core, should as much as possible have the deformation properties and the coherence characteristics of the natural nucleus pulposus in order to respectively have dampening curves compatible with the typical levels of mechanical loads of natural lumbar discs and have resistance to fracturing under applied pressures.

The tissue jacket 100 should have an intrinsic resiliency, or memory, that gives it a tendency to keep its bi-concave nucleus-like shape during its displacement in the cavity and so maintain contact with the natural vertebra endplates. It should also have enough compliance such as not to modify motions and dampening properties of the hydrogel-nucleus.

Alternatively, the nucleus hydrogel 102 may be shaped in a series of independent flexible micro-beads (e.g. spheres containing appropriate fluid for damping effect).

Finally, the above three (3) prostheses P, P' and P'', which are adapted to be installed by an anterior approach on any of the cervical, lumbar, dorsal and thoracic rachis, could also be of a multi-level configuration, that is to cover more than two adjacent vertebrae. The holes defined in the anchoring plates 10/12 and 30/32 or anchoring extensions 106/108 may be vertically elongated (oblong) to allow for some adjustment in the positioning of the prosthesis P/P'/P'' and so that the latter may be used with patients of various vertebra configurations and sizes:

Therefore, the prosthesis of the present invention constitutes a system that attaches two vertebrae together while allowing for relative movements, e.g. pivoting, translational or other, between these vertebrae and while providing some spring force or damping therebetween.

What is claimed is:

1. A disc prosthesis for use on a pair of adjacent vertebrae, wherein the pair of adjacent vertebrae includes an upper vertebra and a lower vertebra, said disc prosthesis comprising:
   upper and lower plates adapted to be mounted respectively to adjacent upper and lower vertebrae;
   a linking joint linking said upper and lower plates, said linking joint comprising an anterior guillotine-type joint having engaged upper and lower members adapted for sliding relative movements therebetween; and
   a damping mechanism adapted to act on said linking joint, said linking joint and said damping mechanism being adapted to allow for limited biased relative movements between the upper and lower vertebrae.

2. A disc prosthesis as defined in claim 1, wherein said upper and lower plates are adapted to extend anteriorly of the vertebrae, said upper and lower plates being integrally connected respectively to said upper and lower members of said linking joint.

3. A disc prosthesis as defined in claim 1, wherein said upper and lower plates define holes, threaded fasteners being provided for engagement through said holes and anteriorly into the vertebrae for securing said plates to the vertebrae.

4. A disc prosthesis as defined in claim 3, wherein said holes are vertically elongated for allowing said prosthesis to be used with various sizes of vertebrae.

5. A disc prosthesis as defined in claim 1, wherein one of said upper and lower members defines a U-shaped recess with the other one of said upper and lower members defining an extension adapted to be slidably received in said U-shaped recess such that said upper and lower members are slidably displaceable along a direction substantially within a plane of said plates.

6. A disc prosthesis as defined in claim 5, wherein said U-shaped recess is provided laterally with guideways extending parallel to said direction and slidably receiving side longitudinal edges of said extension for allowing slidable relative movement between said upper and lower members.

7. A disc prosthesis as defined in claim 6, wherein said linking joint provides a stop for limiting an extension of said upper and lower members relative to each other along said direction.

8. A disc prosthesis as defined in claim 1, wherein said damping mechanism comprises at least one spring acting on said upper and lower members for biasing said linking joint towards an at rest position thereof.

9. A disc prosthesis as defined in claim 8, wherein said spring is located between said upper and lower plates.

10. A disc prosthesis as defined in claim 6, wherein said damping mechanism comprises at least one spring acting on said upper and lower members for biasing said linking joint towards an at rest position thereof.

11. A disc prosthesis as defined in claim 10, wherein the at least one spring is located in one or more of the guideways.

12. A disc prosthesis for use on a pair of adjacent vertebrae, wherein the pair of adjacent vertebrae includes an upper vertebra and a lower vertebra, said disc prosthesis comprising:
   upper and lower plates adapted to be mounted respectively to adjacent upper and lower vertebrae;

a linking joint for linking said upper and lower plates, wherein said linking joint provides a stop for preventing a complete withdrawal of said upper and lower plates from each other, and said linking joint comprising an anterior guillotine-type joint having engaged upper and lower members adapted for sliding relative movements therebetween; and a damping mechanism adapted to act on said linking joint, said linking joint and said damping mechanism being adapted to allow for limited biased relative movements between the upper and lower vertebrae.

13. A disc prosthesis as defined in claim 12, wherein said upper and lower plates are adapted to extend anteriorly of the vertebrae, said upper and lower plates being integrally connected respectively to said upper and lower members of said linking joint.

14. A disc prosthesis as defined in claim 12, wherein said upper and lower plates define holes, threaded fasteners being provided for engagement through said holes and anteriorly into the vertebrae for securing said plates to the vertebrae.

15. A disc prosthesis as defined in claim 12, wherein said damping mechanism comprises at least one spring acting on said upper and lower members for biasing said linking joint towards an at rest position thereof.

* * * * *